DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED FEBRUARY 4, 1975

931 O.G. 9

T931,001

PROCESS OF DYING USING MONOAZO DISPERSE DYES

Abraham Reife, 60 Oakside Drive, Toms River, N.J. 06042, and Grady Malcolm O'Neal, 188 Garfield Ave., Island Heights, N.J. 07904

Continuation of application Ser. No. 88,240, Nov. 9, 1970, which is a continuation-in-part of application Ser. No. 773,325, Nov. 4, 1968, both now abandoned. This application Jan. 16, 1973, Ser. No. 394,377

Int. Cl. D06p *3/82*

U.S. Cl. 8—21 C

No Drawing. 31 Pages Specification

Improvement in dyeing permanent press fabrics which comprises using a dyestuff of the formula

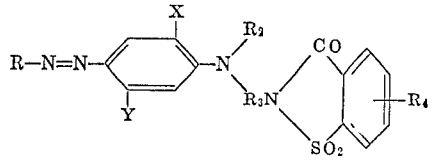

wherein R is the residue of a diazotizable amine free from water solubilizing groups, X is hydrogen, alkyl, alkoxy or halogen; Y is hydrogen, alkyl, alkoxy, halogen or acylamino and $R_2$ is hydrogen or alkyl, hydroxy alkyl, cyano alkyl, alkoxy alkyl, aryloxy alkyl, acyloxy alkyl or halo alkyl; $R_3$ is an alkylene and $R_4$ is hydrogen, nitro, halogen or —CH=CH—CH=CH—. The fabrics thus dyed have excellent fastness properties.